United States Patent [19]

Pazemenas et al.

[11] Patent Number: 4,470,758

[45] Date of Patent: Sep. 11, 1984

[54] INTRAVENOUS FLUID PUMP MONITOR

[75] Inventors: Vytas V. Pazemenas, Newark; Edward G. Solomon, Menlo Park, both of Calif.

[73] Assignee: Oximetrix, Inc., Mountain View, Calif.

[21] Appl. No.: 320,528

[22] Filed: Nov. 12, 1981

[51] Int. Cl.³ .............................................. F04B 21/00
[52] U.S. Cl. ........................................ 417/63; 604/51; 604/245
[58] Field of Search ................ 222/63, 637, 638, 639, 222/642, 643; 417/12, 42–43, 45, 63; 604/34, 50–52, 153, 245–246, 250, 253

[56] References Cited

U.S. PATENT DOCUMENTS

4,137,011  1/1979  Rock .................................... 417/22

Primary Examiner—Edward M. Coven
Attorney, Agent, or Firm—Lyon & Lyon

[57] ABSTRACT

A microprocessor-based controller for regulating the operation of a fluid pump motor is disclosed, wherein the controller includes a protection circuit which prevents fluid over- or under-delivery conditions from occurring by shutting down the pump motor whenever the actual speed of the pump motor differs from a desired pump motor speed by more than a predetermined amount. A simulation means interconnected with the protection circuit simulates fluid over- or under-delivery conditions to test the accuracy of protection circuit operation.

2 Claims, 10 Drawing Figures

INTRAVENOUS FLUID PUMP MONITOR

TECHNICAL FIELD

The present invention is directed to a system for monitoring the operation of a parenteral fluid delivery pump and more particularly concerns a system which compares the rotational speed of a pump stepping motor with an optimum speed setting representing a desired fluid delivery rate in order to provide an indication of unacceptable fluid over-or under-delivery conditions.

BACKGROUND ART

Considerable attention has been focused in recent years on intravenous and intraarterial delivery of fluids to patients. Precision control over the rate at which such parenteral delivery occurs is of critical importance, inasmuch as improper administration of fluids can retard the recovery of patients or, in extreme situations, lead to further injury or even death. Early parenteral delivery systems relied on gravity flow to transfer fluid from a fluid container or reservoir to the patient. Attempts to accurately regulate gravity flow, however, proved difficult because the pressure forcing the fluid between the reservoir and the patient decreased as the fluid level within the reservoir dropped during the delivery operation. Thus, delivery rates in gravity-flow systems tended to vary in an unacceptable manner.

More recent parenteral delivery systems have employed pump motors in an effort to increase fluid delivery rate accuracy. Often, the pump motors comprise stepping motors which drive plunger or piston-like fluid pumps in response to suitable stepping motor control procedures. These procedures are highly compatible with the precision control requirements of parenteral administration because they provide the necessary degree of accuracy and are capable of implementation through reliable and efficient microprocessor programming techniques. U.S. Pat. Nos. 4,037,598 issued to Georgi on July 26, 1977; 3,994,294 issued to Knute on Nov. 30, 1976; 3,985,133 issued to Jenkins et al on Oct. 12, 1976, and 3,736,930 issued to Georgi on June 5, 1973 all disclose intravenous delivery systems wherein stepping motors are utilized in conjunction with camming mechanisms and pumping structures to achieve accurate delivery rate control. Despite the advantages offered by prior art systems, however, certain improvements in the delivery of fluid from a stepping motor-driven fluid pump can be made. For example, it is highly beneficial to provide some means for monitoring the operation of the stepping motor in order to insure that the stepping motor does not "run-away" or deviate from a preselected operating speed by more than a predetermined amount. In this manner, over- or under-delivery of fluid to the patient, as well as the risk of serious injury attendant therewith, can be avoided.

DISCLOSURE OF THE INVENTION

It is accordingly the object of the present invention to furnish a control procedure for monitoring the operation of a pump motor in a parenteral fluid delivery system.

It is another object of the present invention to furnish a means for monitoring the operation of a parenteral fluid pump motor wherein a measure of the actual fluid delivery rate is obtained by detecting the pump motor speed and any deviation in pump motor speed in excess of a predetermined amount is subsequently used to provide a warning of fluid over- or under-delivery conditions.

It is yet another object of the present invention to construct a pump motor controller having a protection circuit which continuously compares the rotational speed of the pump motor with a predetermined optimum speed setting representing a desired fluid delivery rate in order to provide a warning of fluid over- or under-delivery conditions.

It is an additional object of the present invention to construct a pump motor controller having a protection circuit which functions to shut down the pump motor whenever the ratio between the actual pump motor speed and an optimum pump motor speed representing a desired fluid delivery rate exceeds predetermined limits.

It is a further object of the present invention to construct a pump motor controller having a microprocessor for implementing motor control procedures and a protective circuit which independently detects errors in the operation of the microprocessor.

It is an object of the present invention to provide a protection circuit for a microprocessor-based fluid pump motor controller wherein the protection circuit functions to shut down the pump motor whenever fluid over- or under-delivery conditions are encountered, the protection circuit including means to simulate fluid over- or under-delivery conditions to test the accuracy of protection circuit operations.

These and other objects of the present invention are achieved by a microprocessor-based motor controller employing a protection circuit capable of detecting pump motor run-away, microprocessor malfunction and programming errors. The prevention circuit includes a first comparison means which continuously measures actual pump motor rotational speed against an optimum speed setting representing the desired fluid delivery rate. Whenever the actual pump motor speed deviates from the optimum pump motor speed by more than a predetermined amount, a first warning signal is generated and the pump motor is shut down. The accuracy of the first comparison means can be tested using a selected motor controller test procedure. A second comparison means in the prevention circuit compares the fixed frequency of an output signal from the microprocessor with the frequency of an independent reference signal. Whenever the frequency of the output signal from the microprocessor deviates by more than a predetermined amount from the frequency of the independent reference signal, such as occurs when the microprocessor is malfunctioning, a second warning signal is generated. If subsequent reset of the microprocessor does not correct the malfunction, a suitable alarm will follow.

BRIEF DESCRIPTION OF THE DRAWINGS

The various objects, features and advantages of the present invention can best be understood by examining the following Brief Description Of The Drawings and Best Mode For Carrying Out The Invention, wherein.

BEST MODE FOR CARRYING OUT THE INVENTION

Figure 1:
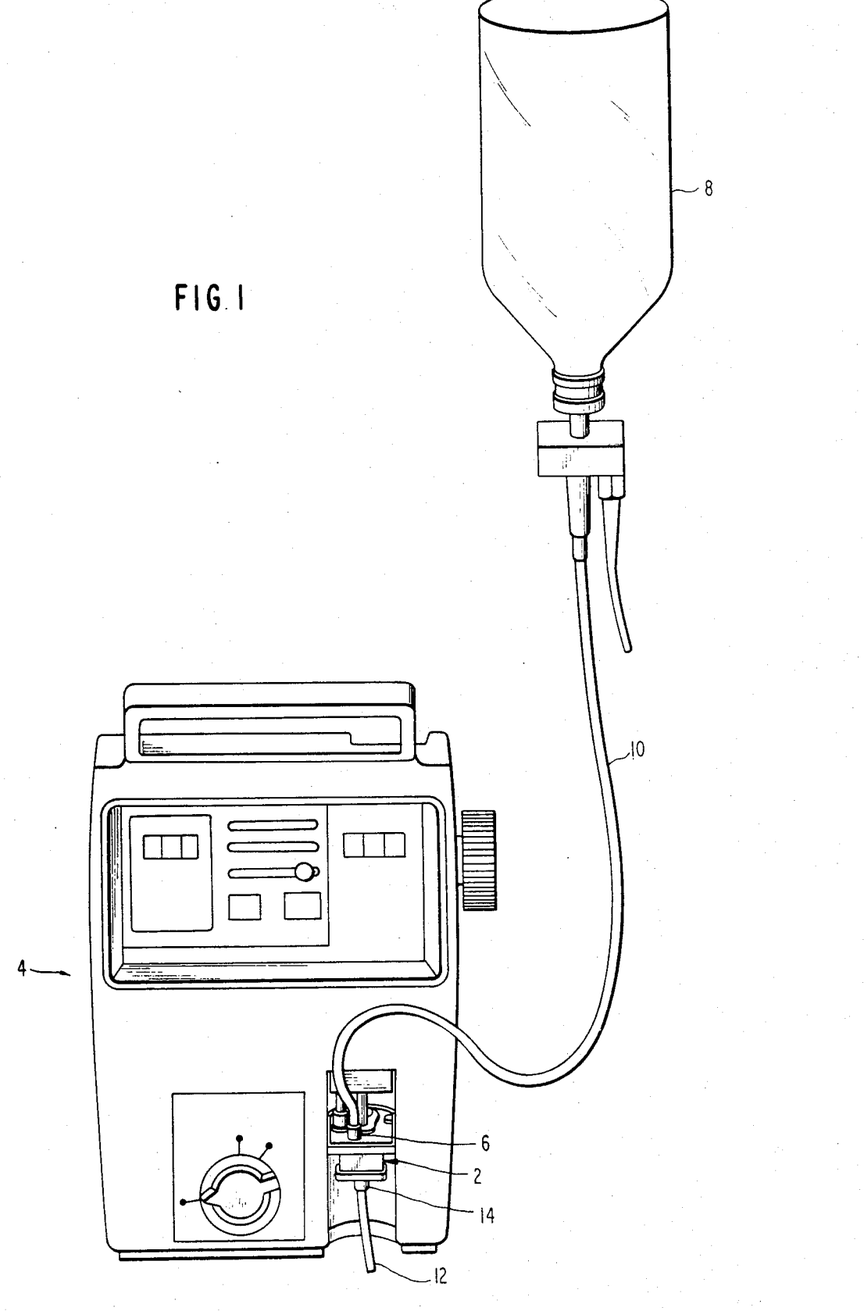
FIG. 1 is a perspective view illustrating the parenteral delivery system of the present invention.
Figure 2:
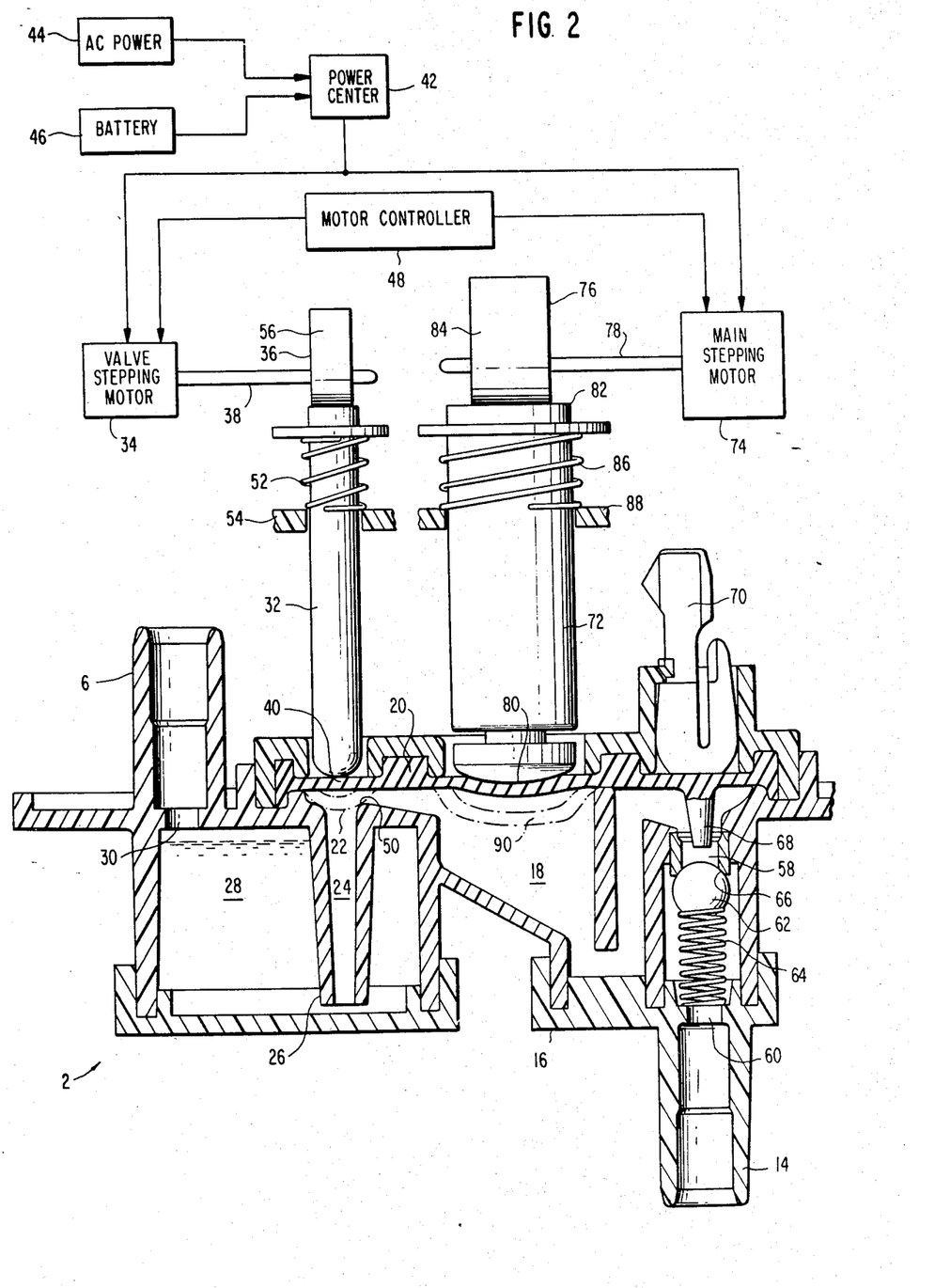
FIG. 2 is a cross-sectional view of a pumping cassette, valve stepping motor and main stepping motor utilized in the parenteral delivery system of FIG. 1.

One type of parenteral fluid metering device for delivering controlled amounts of fluid to a patient is schematically illustrated in FIGS. 1 and 2. Basic and improved embodiments of the fluid metering device are disclosed in co-pending application Ser. Nos. 174,666 and 278,954, respectively filed Aug. 1, 1980 and June 30, 1981. Both of these co-pending applications are assigned to the assignee of the present invention and both are incorporated herein by reference. For purposes of understanding the present invention, the following brief description of the improved parenteral fluid metering device of application Ser. No. 278,954 will suffice. Referring first to FIG. 1, the fluid metering device 2 is shown positioned within a metering device control unit 4. An in-flow conduit 6 on fluid metering device 2 is connected to a container of fluid 8 by means of conventional tubing 10. Tubing 12, extending from out-flow conduit 14 of the fluid metering device 2, transfers precise amounts of fluid to the patient being treated in response to actuation of a stepping motor and camming mechanism (not shown in FIG. 1) housed in control unit 4.

Turning to FIG. 2, the construction of the fluid metering device 2, as well as the stepping motor and camming mechanism, is shown in greater detail. Fluid metering device 2 includes a hollow cassette structure 16 having a pumping chamber 18 disposed therein. A resilient diaphragm 20 is secured across the top of pumping chamber 18. An inlet port 22 at one end of passageway 24 formed in gas retention conduit 26 permits fluid to pass from a gas retention chamber 28 into pumping chamber 18. Gas retention chamber 28 in turn fluidically communicates with in-flow conduit 6 through an intermediate passageway 30. A valve actuator 32 operatively connected to valve stepping motor 34 via a cam and shaft mechanism 36, 38 controls the admission of fluid into pumping chamber 18 by displacing a portion 40 of resilient diaphragm 20 positioned above inlet port 22. Current is supplied to valve stepping motor 34 by a power control center 42 which may be alternately connected to an AC power supply 44 or a battery supply 46. Valve stepping motor 34 is driven through a series of incremental steps in response to commands received from motor controller 48, whereupon valve actuator 32 reciprocates to move the diaphragm portion 40 between an open position, as indicated by solid lines in FIG. 2, and a sealing engagement with a valve seat 50 formed around the periphery of inlet port 22, as indicated in phantom in FIG. 2. A biasing means such as spring 52 seated on hollow boss 54 formed in control unit 4 provides the necessary force for urging valve actuator 32 into positive contact with the camming surface 56 of cam 36.

An outlet port 58 is formed in pumping chamber 18 opposite inlet port 22. Outlet port 58 communicates with outlet conduit 14 through an intermediate passageway 60. A ball check 62 is mounted between outlet port 58 and intermediate passageway 60. A biasing means such as spring 64 urges the ball check into sealing engagement with a valve seat 66 formed around the periphery of outlet port 58. A projection 68 formed on resilient diaphragm 20 opposite ball check 62 displaces the ball check from valve seat 66 during pump priming operations. A manual latch valve 70 is used to move projection 68 into contact with the ball check.

Motive power for pumping fluid through the cassette 16 of fluid metering device 2 is supplied by a plunger 72 operatively connected to a main stepping motor 74 via a cam and shaft mechanism 76, 78. Main stepping motor 74 also receives current from power control center 42 under the command of motor controller 48. One end 80 of plunger 72 contacts resilient diaphragm 20 while the remaining end 82 is urged into positive contact with the camming surface 84 of cam 76 by a biasing means such as spring 86 seated on hollow boss 88 of control unit 4. The incremental or step rotation of main stepping motor 74, and hence of cam 76, drives plunger 72 in a reciprocal fashion between a fully retracted position, indicated by solid lines in FIG. 2, and a fully extended position indicated in phantom at 90 in FIG. 2. Resilient diaphragm 20 flexes in response to the reciprocal motion of plunger 72 to periodically vary the volume of pumping chamber 18, thereby providing the pumping action necessary to drive a metered amount of fluid from the pumping chamber into the fluid outflow conduit 14.

Figure 3:
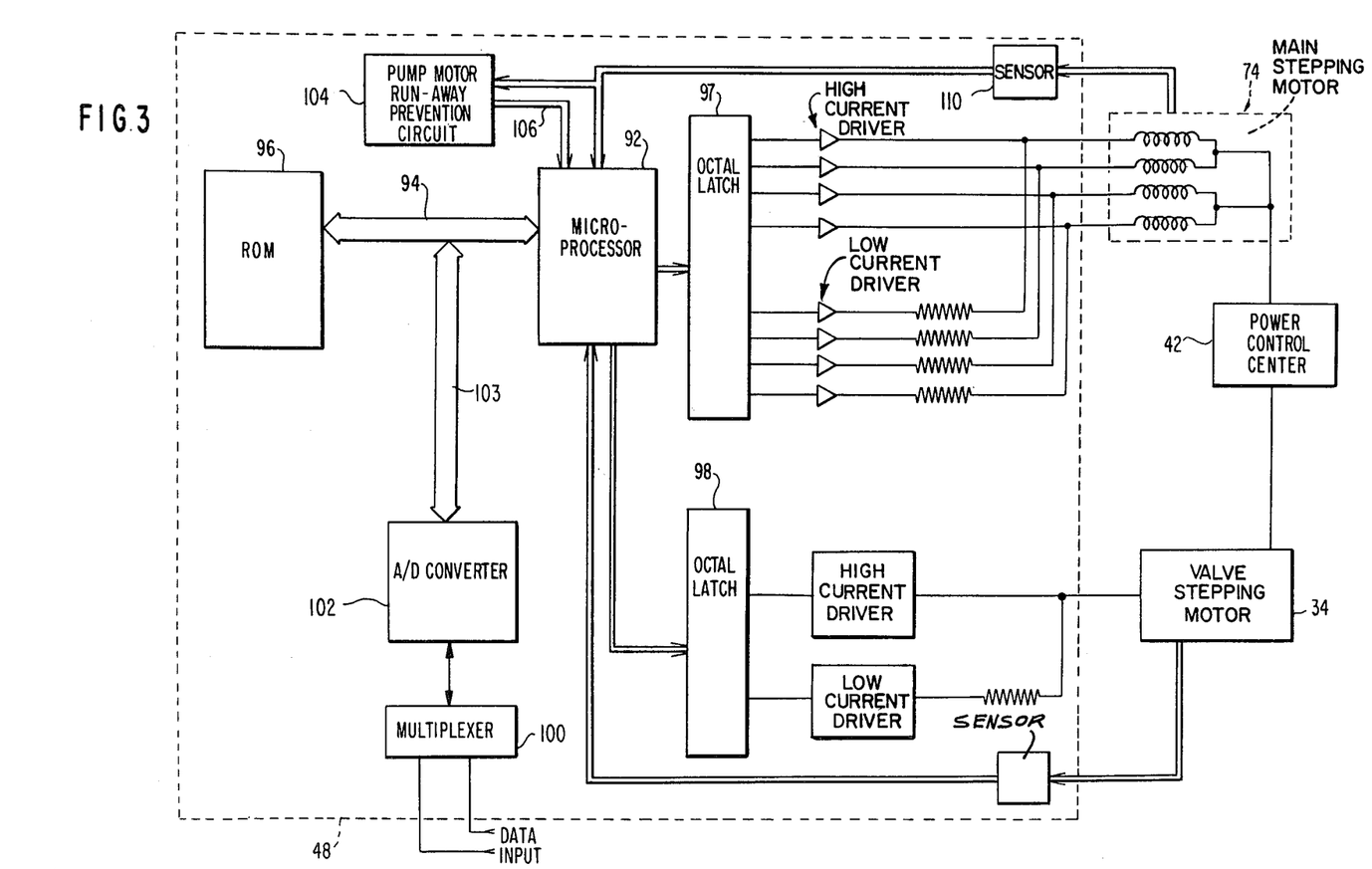
FIG. 3 schematically depicts the motor controller which governs the operation of the valve stepping motor and main stepping motor of FIG. 2.

As previously indicated, valve stepping motor 34 and main stepping motor 74 are both under the command of motor controller 48. The motor controller, which is schematically illustrated in FIG. 3, includes a microprocessor 92 connected by a data link 94 to a read-only-memory 96. Suitable control procedures for the valve stepping motor 34 and the main stepping motor 74 are stored in the read-only-memory 96 and supplied to microprocessor 92 on demand. The microprocessor in turn directs a pair of octal latches 97, 98 to drive the valve stepping motor and the main stepping motor respectively through their incremental steps in accordance with the control procedures stored in the read-only-memory. A multiplexer 100 is connected to various data sensors such as the plunger pressure transducer (not shown) disclosed in aforementioned Ser. No. 278,954. An A/D converter 102 converts the signals from multiplexer 100 into a form useable by microprocessor 92 and feeds the signals so converted to the microprocessor via data link 103. A "watch-dog" or pump motor run-away prevention circuit 104 is tied to the microprocessor via data link 106. The purpose of pump motor run-away prevention circuit 104 is to monitor the activity of the main stepping motor 74 and to provide an alarm when the speed of the main stepping motor exceeds predetermined upper or lower limits, indicating the occurrence of potentially dangerous over- or under-delivery conditions. Motor controller 48 and the stepping motor control procedures are disclosed in greater detail in copending application Ser. No. 314,038, filed Oct. 22, 1981, and incorporated herein by reference. Pump motor run-away prevention circuit 104 is disclosed in greater detail below.

The pumping operation of fluid metering device 2 will now be described. Returning to FIG. 2, it can be seen that incoming fluid transmitted by tubing 10 to fluid inflow conduit 6 passes into gas retention chamber 28, whereupon any gases otherwise present in the fluid are prevented from reaching pumping chamber 18 by the presence of gas retention conduit 26. Liquid free of gas bubbles next travels from the gas retention chamber 28 through passageway 24 to inlet port 22. During the refill phase of each pumping cycle, valve stepping motor 34 operates to reciprocate valve actuator 32 upwardly, allowing fluid free of gas bubbles to pass through the inlet port into pumping chamber 18. Shortly thereafter, plunger 72 is reciprocated upwardly by main stepping motor 74 to increase the volume and reduce the pressure within pumping chamber 18, aiding the flow of fluid through the inlet port. The spring-loaded ball check 62 seated against valve seat 66 effectively closes off outlet port 58 while valve actuator 32 is in the open position. Accordingly, no fluid can leak into fluid out-flow conduit 14 during the refill phase of the pumping cycle and precise control over the amount of fluid to be pumped from pumping chamber 18 is maintained. After a brief interval in the open position, valve actuator 32 is moved to a closed position. Plunger 72 is then reciprocated downwardly as described hereinabove to decrease the volume within pumping chamber 18. As the volume within the pumping chamber decreases, the pressure within the pumping chamber increases to overcome the bias exerted by spring 64 against ball check 62 and a precise amount of metered fluid is pumped from pumping chamber 18 through out-flow conduit 14 and tubing 12 to the patient. The fluid pressure necessary to open ball check 62 is determined in large part by the spring constant of spring 64.

It should here be noted that the fluid metering device 2 of FIG. 2 operates in one of three distinct modes, each of which modes has a particular or desired fluid delivery rate associated therewith. In the first or normal operating mode of the fluid metering device, fluid is delivered at a preselected rate set into motor controller 48 via a thumbwheel switch (not shown) on control unit 4 of FIG. 1. This preselected rate may, for example, vary from 0 to 999 milliliters per hour depending upon the needs of the individual patient receiving the fluid. The second operating mode of the fluid metering device is a keep-vein-open mode designed to deliver a minimal amount of fluid to the venous entrance site in the patient when the first or normal operating mode has been completed or when the fluid level in reservoir 8 reaches a predetermined lower limit, thereby preventing clotting or occlusion of the IV needle (not shown) at the end of tubing 12. The keep-vein-open mode is initiated in response to either a low fluid level alarm (not shown) or an end of dosage indication, whereupon motor controller 48 drives main stepping motor 74 at a predetermined low speed to provide a predetermined low or KVO delivery rate. The final operating mode of the fluid metering device is the stop mode in which main stepping motor 74 is deenergized and no fluid is delivered to the patient. The stop mode, of course, is characterized by a zero fluid delivery rate.

Figure 4:
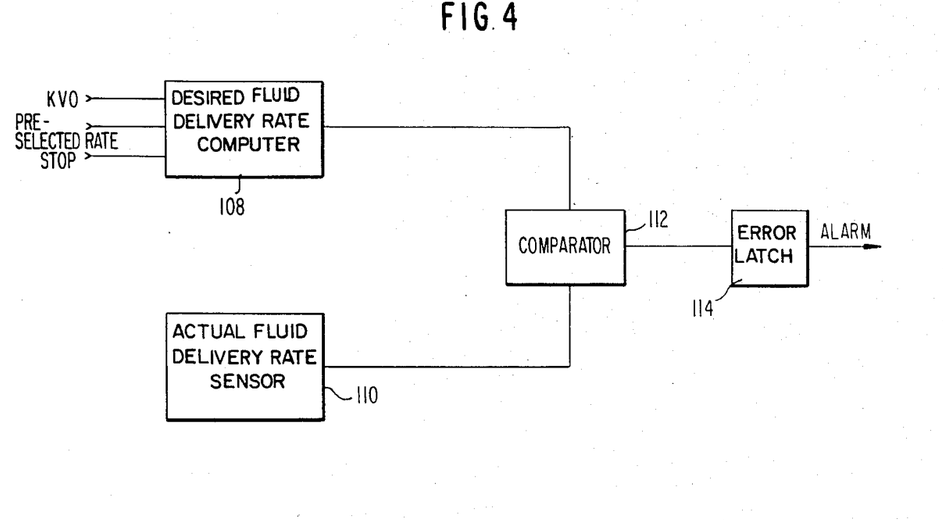
FIG. 4 schematically depicts the pump motor runaway prevention circuit of the present invention.

The pump motor run-away prevention circuit discussed in connection with FIG. 3 is schematically depicted in FIG. 4. Pump motor run-away prevention circuit 104 includes a computing means 108 supplied with either a preselected rate setting, KVO signal or a stop signal representing the desired rate of fluid delivery from fluid metering device 2. Computing means 108 thereafter generates a first indicator having at least one parameter which varies in accordance with the value of the desired fluid delivery rate. A second indicator having at least one parameter which varies in accordance with the value of the actual rate of fluid delivery from the fluid metering device is generated by a sensing means 110. The first and second indicators are simultaneously directed to a comparator means 112 and compared with one another. If this comparison is within acceptable limits, i.e., if the actual fluid delivery rate has not deivated from the desired fluid delivery rate by more than a predetermined amount, safe fluid delivery conditions are assumed and motor controller 48 continues to drive main stepping motor 74 in normal fashion. If, by way of contrast, the actual fluid delivery rate does deivate from the desired fluid delivery rate by more than the predetermined amount, evidencing a potentially dangerous fluid over- or under-delivery condition, comparator means 112 will not detect a proper comparison between the first and second indicators. An error signal is then generated in the comparator means and supplied to an error latch 114. In response to the error signal, error latch 114 outputs an alarm signal which may then be used to turn off the voltage supplied by power control center 42 to main stepping motor 74, shutting the main stepping motor down. The alarm signal from the error latch may also serve to activate an audio or visual warning of the fluid over- or under-delivery condition.

Figure 5:
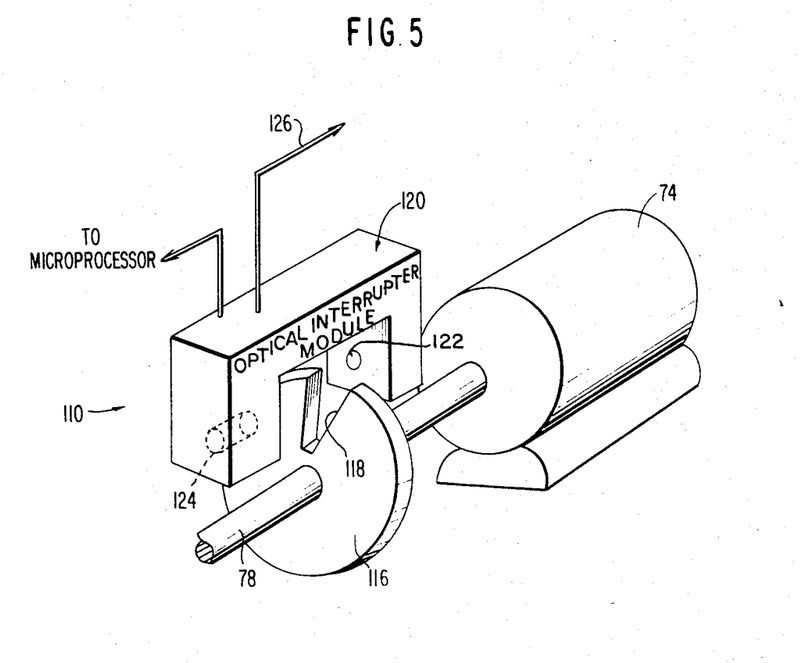
FIG. 5 illustrates an electromechanical means for measuring the rotational frequency or speed of the main stepping motor disclosed in FIG. 2.

The comparison scheme of FIG. 4 may be implemented in either software or dedicated hardware form. A circuit structure specifically designed for dedicated hardware implementation of the comparison scheme is illustrated in FIGS. 5 through 8. FIG. 5 in particular discloses one type of electromechanical arrangement suitable for use as the sensing means 110 of FIG. 4, wherein the rotational frequency or speed of the main stepping motor 74 is measured to provide an indication of the actual fluid delivery rate of the fluid metering device. A flange or flag 116 having a slot 118 formed therein is positioned on the shaft 78 connecting main stepping motor 74 with cam 76. An optical interruptor module 120 comprising an LED 122 positioned on one side of flange 116 and a photodetector 124 positioned opposite LED 122 on the other side of flange 116 is connected to the microprocessor 92 in motor controller 48. During the operation of fluid metering device 2, LED 122 is illuminated. As main stepping motor 74 is driven through its incremental steps, the presence of flange 116 serves to block radiation generated by LED 122 from reaching photodetector 124. Once during each revolution of the main stepping motor, however, slot 118 will move into alignment with the optical interruptor module 120 and radiation leaving LED 122 will impinge upon photodetector 124. The resultant output from the photodetector is used by the optical interruptor module to generate a FLAG pulse on lead 126. Continued rotation of main stepping motor 74 produces a train of FLAG pulses on lead 126, with each pulse in the train representing a single revolution of the main stepping motor. Thus, the FLAG pulse train serves as a count for determining the number of revolutions made by the main stepping motor during any given period of time. The total number of revolutions during the given time period in turn corresponds to the actual rate of fluid delivery from fluid metering device 2, and can be compared with a count representing the desired fluid delivery rate in order to determine whether the actual fluid delivery rate is within acceptable limits.

Figure 6:
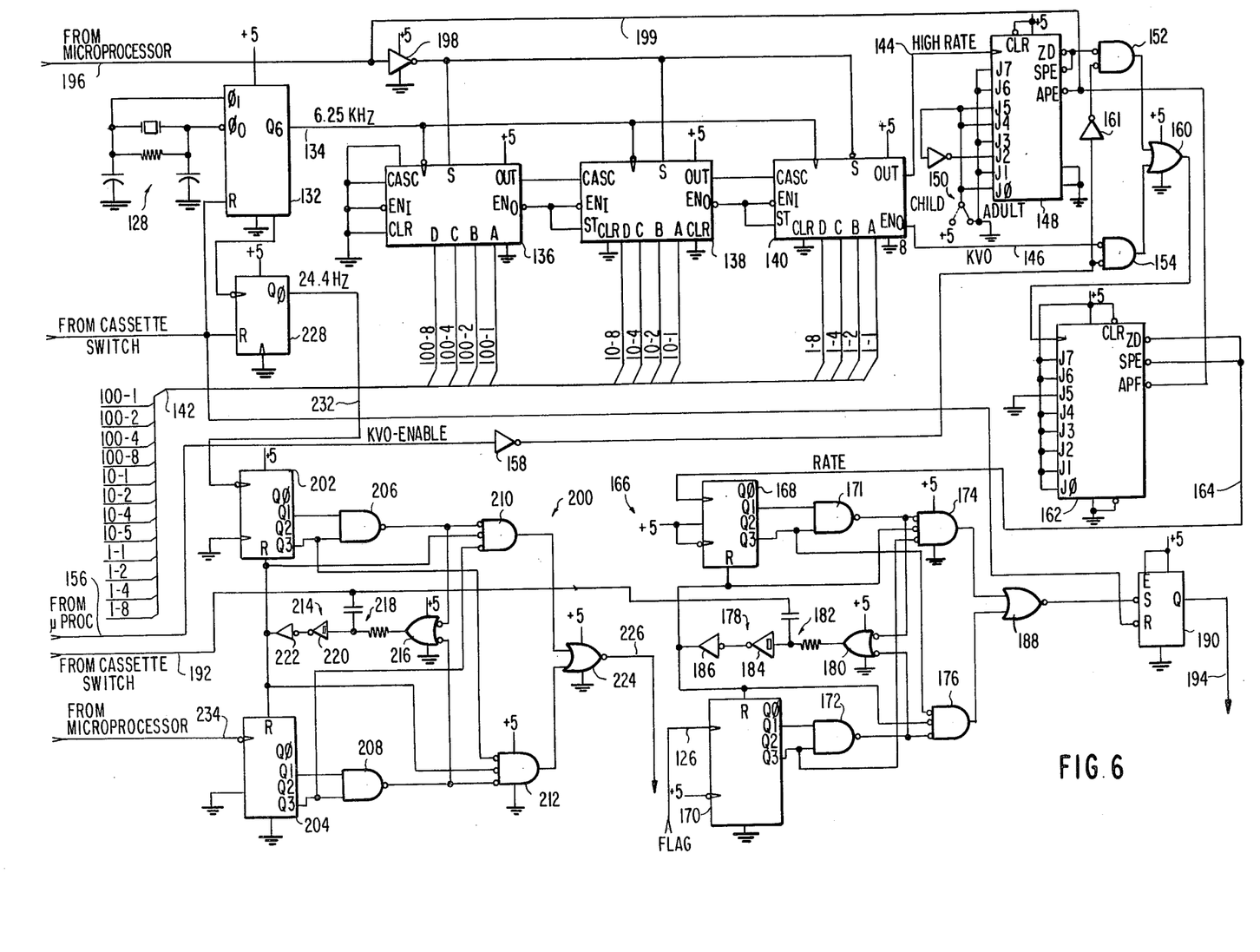
FIG. 6 is a detailed circuit diagram showing a dedicated hardware version of the run-away prevention circuit of FIG. 4.

FIG. 6 illustrates a dedicated hardware circuit capable of both generating the count representing the desired fluid delivery rate and comparing the count so generated with the count from the optical interruptor module 120 of FIG. 5. The desired fluid delivery rate count is derived by dividing a base count obtained from an independent clock 128. Independent clock 128 includes a 400KHz oscillator/counter 132 which provides a 6.25KHz signal on lead 134. The independent operation of oscillator/counter 132 relative to the internal clock of microprocessor 92 prevents any microprocessor malfunction from affecting the reliability of the run-away prevention circuit operation. The 6.25KHz signal on lead 134 is used to clock a series of rate multipliers 136, 138 and 140. The data inputs to the rate multipliers are supplied via data line 142 with signals respectively representing the hundreds, tens, and ones digits of the preselected rate setting on the control unit thumbwheel switch (not shown). The value of the hundreds, tens and ones digits are also read from the thumbwheel switch by microprocessor 92 (not shown in FIG. 6). Rate multipliers 136, 138 and 140 are connected to one another in conventional cascade fashion, thereby providing lead 144 with a high rate output having a relatively high frequency proportional to the preselected rate setting. In the preferred embodiment of the present invention, this relatively high frequency may be expressed as:

$$f_h = \text{Rate Setting}/1{,}000 \times 6.25 \text{KHz}$$

where Rate Setting represents the entry on the thumbwheel switch. It should also be noted that a fixed, low frequency or KVO output is supplied by rate multipliers 136, 138 and 140 along lead 146. The latter output is used as a reference when fluid metering device 2 is in a keep-vein-open mode.

The high rate output on lead 144 passes to a first dividing counter 148 and is converted to an intermediate rate output having an intermediate frequency still proportional to the preselected rate setting. This intermediate frequency may be varied by a factor of ten depending upon the position of switch 150. Hence, the pump motor run-away prevention circuit of the present invention may be accomodated to pediatric fluid delivery rates, which are generally smaller than adult fluid delivery rates by a factor of ten. The intermediate rate output generated by counter 148 serves as one input to a NOR gate 152, while the KVO output on lead 146 serves as one output to NOR gate 154. The remaining inputs to the two NOR gates are supplied by a KVO-ENABLE logic signal on lead 156 from microprocessor 92 in accordance with the operating mode of the fluid metering device. Assuming for the moment that the fluid metering device is operating in a normal mode to administer fluid at the preselected delivery rate, the KVO-ENABLE signal from microprocessor 92 is low. Inverter 158 switches the KVO-ENABLE signal high, whereupon NOR gate 154 is disabled and no KVO output from rate multiplier 140 reaches OR gate 160. The same high signal which disables NOR gate 154 is also passed through inverter 161 before reaching NOR gate 152, with the net result that NOR gate 152 is enabled to pass the intermediate rate output from counter 148 to OR gate 160. Subsequently, the intermediate rate output drives a second dividing counter 162 such as a divide-by-224 counter to provide a RATE pulse train having a frequency suitable for comparison with the frequency of the FLAG pulse train from the optical interruptor module 120 of FIG. 4. The RATE pulse train frequency is, of course, proportional to the desired rate of fluid delivery from fluid metering device 2, in this case the preselected rate associated with the normal operating mode of the fluid metering device.

When, in contrast, fluid metering device 2 is operating in a keep-vein-open mode, the high KVO-ENABLE signal supplied from microprocessor 92 disables NOR gate 152 to block the intermediate rate output leaving counter 148 while NOR gate 154 is enabled to pass the KVO output to OR gate 160. Counter 162 again provides a RATE pulse train for comparison purposes, but the frequency of the RATE pulse train is now proportional to the KVO rate associated with the keep-vein-open mode.

The RATE pulse train generated by counter 162 is supplied via lead 164 to a first or run-away comparator means 166 comprising a pair of binary counters 168 and 170. The clock input to binary counter 168 is connected to receive the RATE pulse from lead 164, while the clock input to binary counter 170 is connected to receive the FLAG pulse train from lead 126 of optical interruptor module 120 (not shown in FIG. 6). Binary counters 168 and 170 are multi-stage components such as National Semiconductor CD4520 counters, each having at least four output stages $Q_0$, $Q_1$, $Q_2$ and $Q_3$. The $Q_1$ and $Q_3$ output of each binary counter 168, 170 is connected to an associated one of a pair of NAND gates 171, 172. NAND gates 171, 172 in turn respectively supply one input to triple input NOR gates 174, 176. The second input to NOR gate 174 is connected to the $Q_3$ output of binary counter 170, while the second input to NOR gate 176 is connected to the $Q_3$ output of binary counter 168. Run-away comparator means 166 also comprises a reset circuit 178 including a NAND gate 180 which is driven by the output of either NAND gate 171 or NAND 172 to supply a RESET pulse through RC delay 182 and series inverters 184, 186. The RESET pulse operates to reset binary counters 168 and 170, and also furnishes the remaining input for each triple-input NOR gate 174 and 176. The NOR gates 174 and 176 are connected through NOR gate 188 to the inverting input of an error latch 190.

The operation of run-away comparator 166 will now be described. Insertion of the fluid metering device cassette 16 (not shown in FIG. 6) into control unit 4 triggers a switch (not shown) to provide a high output on lead 192. This high output passes through RC delay 182 in series inverters 184, 186 of reset circuit 178 and, after an interval of time determined by the RC time constant of delay 182, acts to reset both binary counters 168 and 170. Thereafter, the incoming RATE pulse train on lead 164, representing the desired rate of fluid delivery from the fluid metering device, clocks counter 168 through a series of output states as a function of the RATE pulse train frequency. The $Q_0$–$Q_3$ outputs of counter 168 are consequently switched between various combinations of high and low values to provide a binary count of the RATE pulses which reach counter 168 following the RESET pulse. That is, the first RATE pulse switches the $Q_0$ output of counter 168 high to form a 0001 binary count, the second RATE pulse switches the $Q_1$ output of counter 168 high to form a 0010 binary count, the third RATE pulse switches both the $Q_0$ and $Q_1$ outputs of counter 168 high to form a 0011 binary count, and so on. A similar binary count appears on the $Q_0$–$Q_3$ outputs of binary counter 170 in response to the FLAG pulse train on lead 126, which FLAG pulse train represents the actual rate of fluid delivery from the fluid metering device.

Throughout the first nine RATE pulses, the $Q_1$ and $Q_3$ outputs of binary counter 168 alternate between high and low values as previously indicated. Simultaneous switching of the $Q_1$ and $Q_3$ outputs to high values, however, does not occur until the tenth RATE pulse, i.e., until counter 168 reaches the binary count 1010. The output from NAND gate 171 accordingly remains high to disable triple-input NOR gate 174 for each of the first nine RATE pulses, and the signal from NOR gate 174 to NOR gate 188 remains low. FLAG pulses contemporaneously arriving on lead 126 from the optical interruptor module 120 of FIG. 4 likewise switch the $Q_1$ and $Q_3$ outputs of binary counter 170 between alternating high and low values, but until the occurance of the tenth FLAG pulse following the counter reset, the output of NAND gate 172 also remains high to disable triple-input NOR gate 176. The attendant low output from NOR gate 176, together with the aforementioned low output from NOR gate 174, force NOR gate 188 high to prevent the setting of the error latch 190.

When the tenth RATE pulse clocks binary counter 168, NAND gate 171 is driven low, removing an otherwise disabling input to NOR gate 174. At the same time, the output of NAND gate 180 in reset circuit 178 is switched high to generate another RESET pulse. The presence of RC delay 182 in the reset circuit prevents the RESET pulse from reaching binary counters 168 and 170 for a short interval. During this short interval, the status of binary counter 170 is monitored. If at least eight FLAG pulses have appeared on lead 126, the $Q_3$ output of counter 170 will be high and NOR gate 174 remains disabled despite the low output from NAND gate 171. The high output from NOR gate 188 prevents setting of the error latch 190, keeping the error latch Q output low. If, on the other hand, a motor or microprocessor malfunction slows the operation of main stepping motor 74 sufficiently, less than eight FLAG pulses will have clocked counter 170 and the $Q_3$ output thereof will remain low. NOR gate 174 will then switch high to drive the output of NOR gate 188 low, causing error latch 190 to generate a high Q output which may be supplied on lead 194 to a voltage regulator (not shown) in power control center 42. The high Q output from the error latch, which serves as an alarm signal indicative of slow motor speed and hence of potential fluid under-delivery conditions, causes the voltage regulator to output zero volts to main stepping motor 74. This zero voltage output, of course, shuts down main stepping motor 74 to stop the delivery of fluid from fluid metering device 2. Microprocessor 92 can, if desired, monitor lead 194 in order to generate an error code when the Q output of error latch 190 is high. The high Q alarm signal may also trigger an audio or visual alarm circuit (not shown), alerting the operator of the fluid metering device to the existence of under-delievery conditions.

Where fluid over-delivery conditions exist, FLAG pulses arrive at binary counter 170 with greater frequency than the RATE pulses arriving at binary counter 168. Hence, counter 170 will be the first counter to reach a binary ten count, driving the output of NAND gate 172 low and forcing reset circuit 178 to generate a delayed RESET pulse. Unless the $Q_3$ output of counter 168 at this point is high, indicating at least a binary eight count of the incoming RATE pulses, triple-input NOR gate 176 will switch high to drive the output of NOR gate 188 low. Error latch 190 will thereafter output a high Q value to provide an alarm signal as previously described.

Following the short interval defined by the time constant of RC delay 182, binary counters 168 and 170 are reset by the RESET pulse generated in response to the low output from either NAND gate 171 or NAND gate 172. The RESET pulse also disables triple-input NOR gates 174 and 176 during the resetting operation to prevent spurious tripping of the error latch 190. Binary counting of both the FLAG and RATE pulses then resumes, with another high Q output from error latch 190 appearing on lead 194 whenever the ratio of the FLAG pulse count to the RATE pulse count falls below 0.8 or rises above 1.25, i.e., whenever the ratio lies outside the range between 8/10 and 10/8. Of course, as long as the FLAG or RATE pulses do not lag behind one another by more than the specified eight-to-ten ratio, i.e., as long as the actual fluid delivery rate does not deviate from the desired fluid delivery rate beyond the predetermined limits, no alarm signal will occur.

Figure 9A:
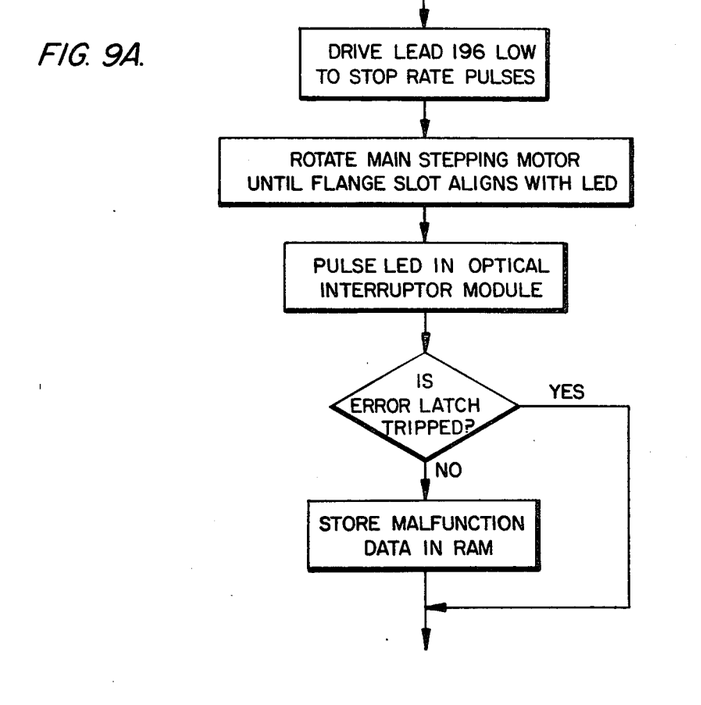
FIGS. 9A and 9B illustrate in flow chart form the program steps employed to stimulate fluid over-delivery and under-delivery conditions during testing of the run-way prevention circuit of FIG. 6.

Microprocessor 92 (not shown in FIG. 6) may be designed to simulate fluid over- or under-delivery conditions in order to test the accuracy of comparator means 166 when fluid metering device 2 is not in use. In the case of a simulated fluid over-delivery condition, lead 196 is driven low by the microprocessor, whereupon inverter 198 supplies the set pin of each rate multiplier 136, 138 and 140 with a high signal to stop the operation of the rate multipliers. Simultaneously, the low signal on lead 196 acts via lead 199 to stop the operation of counters 148 and 162. The RATE pulse train leaving counter 162 effectively ceases, shutting down the operation of binary counter 168 in comparator means 166. Main stepping motor 74 (not shown in FIG. 6) is rotated until the slot 118 in flange 116 is brought into alignment with the optical interruptor module 120 discussed in connection with FIG. 4. LED 122 in the optical interruptor module is then pulsed at an arbitrarily high value by the microprocessor in order to generate a FLAG pulse train. The FLAG pulses clock counter 170 in comparison means 166, generating $Q_1$ and $Q_3$ outputs which drive the output of NAND gate 172 low following the tenth FLAG pulse. Because no RATE pulses are being generated, however, the $Q_3$ output of counter 168 remains low as the output of NAND gate 172 switches low. Thus, a fluid over-delivery condition has been simulated and the output of triple-input NOR gate 174 should switch high, forcing the output of NOR gate 188 low to trip error latch 190 and provide an alarm signal on lead 194. If the alarm signal does not appear, a malfunction in comparator means 166 is indicated and an independent storage device such as a RAM (not shown) in microprocessor 92 may be employed to record this fact. When normal operation of the motor controller is resumed, the malfunction data may be read out of the RAM and used to trigger an audible or visual alarm. A flow chart illustrating fluid over-delivery simulations can be seen in FIG. 9A.

Figure 9B:
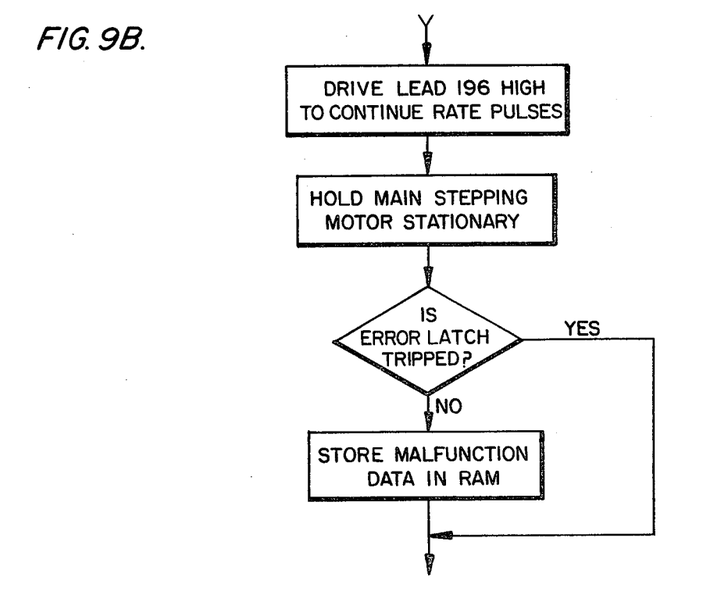

Fluid under-delivery conditions may be simulated as depicted in FIG. 9B by keeping the signal on lead 196 high while holding main stepping motor 74 stationary in order to prevent pulsing of the output from photodetector 124. RATE pulses from the rate multipliers 136–140 and counters 140, 162 accordingly continue to be delivered to comparison means 166 in a normal fashion but the FLAG pulses from the optical interruptor module cease. Subsequent operation of the comparison means should yield an alarm signal indicative of the simulated under-delivery condition, inasmuch as the $Q_3$ output of binary counter 170 should remain low when the binary count of counter 168 reaches ten to trip error latch 190 and generate an alarm signal on lead 194 in the manner previously described. Again, the failure of an alarm signal to appear is indicative of comparison means malfunction and data reflecting such failure can be stored by the microprocessor for later use.

The operation of the microprocessor itself may be monitored with a second or hardware comparison means 200. Hardware comparison means 200 is both structurally and functionally identical to run-away comparison means 168, and includes paired multi-stage binary counters 202, 204 respectively connected to drive a pair of NAND gates 206, 208, which paired NAND gates in turn respectively gate triple-input NOR gates 210, 212 in response to the comparison between the binary count of counters 202 and 204. Reset circuit 214, including NAND gate 216, RC delay 218 and series inverters 220, 222, is connected to reset binary counters 202 and 204 at the end of each ten count sequence. NOR gate 224 connected to NOR gates 210 and 212 supplies a low signal on lead 226 whenever the ratio between the binary count accumulated in counter 202 and binary count accumulated in counter 204 falls outside of the predetermined 8/10–10/8 range. A counter 228 is clocked by a signal on lead 230 from counter 132 to generate an independent clock signal having a frequency, for example, of 195 Hz. The independent clock signal is connected via lead 232 to the clock input of binary counter 202 while a fixed frequency signal from the microprocessor, optimally having the same 195 Hz frequency as the independent clock signal, is connected via lead 234 to the clock input of binary counter 204. As long as the microprocessor is functioning properly, the frequency of the signal clocking counter 204 should track the independent clock signal within the limits set by hardware comparison circuit 200, and the output of NOR gate 224 should remain high. If, on the other hand, some hardware malfunction in the microprocessor occurs, or if some programming error exists in the microprocessor software, the microprocessor will generally be effected to the extent that the frequency of the fixed frequency signal clocking counter 204 increases or decreases beyond the point necessary to drive the output of NOR gate 224 low. This low NOR gate output can then be used to initiate protective measures in the motor controller, such as resetting the microprocessor or sounding an alarm.

Figure 7:
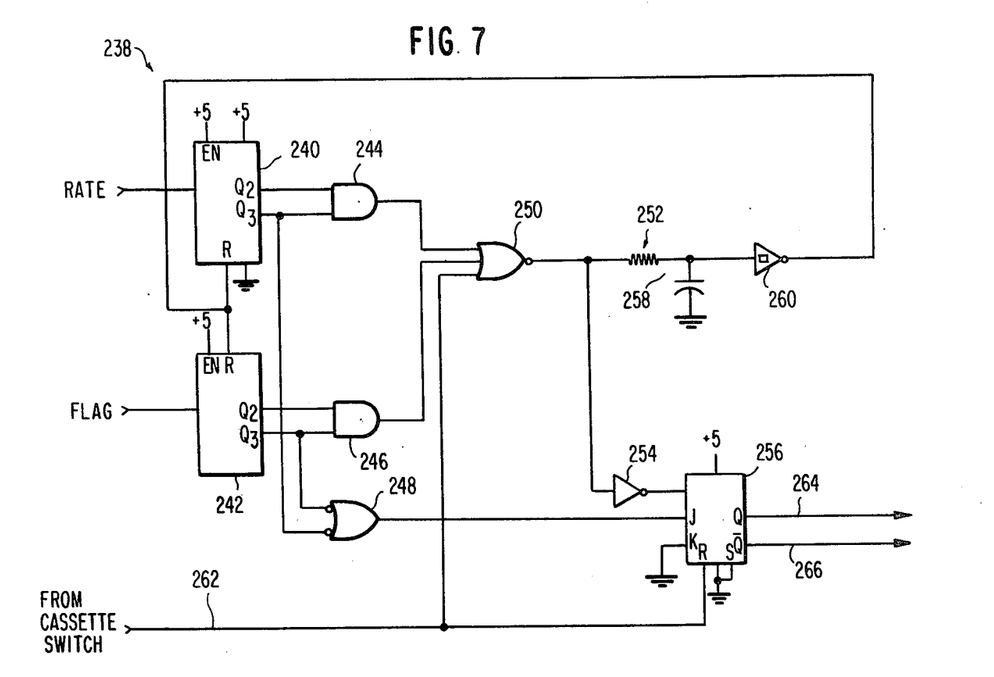
FIG. 7 is an alternate embodiment of a comparator circuit for use with the pump motor run-away prevention circuit of FIG. 6.

An alternate embodiment of a comparator means suitable for use as either the first or second comparator means 166, 200 of FIG. 6, can be seen in FIG. 7. Comparator means 238 includes a pair of multi-stage binary counters 240, 242 which, when comparator means 238 is employed in lieu of runaway comparator means 166 in FIG. 6, are respectively clocked by the RATE pulse train and the FLAG pulse train. Both of the binary counters 240, 242 have at least four output stages, $Q_0$–$Q_3$, and the $Q_2$ and $Q_3$ outputs of each counter are connected to an associated one of a pair of AND gates 244, 246. In addition, the $Q_3$ output from each binary counter is connected to one input of a NAND gate 248. The outputs of AND gates 244, 246 are supplied to a triple-input NOR gate 250. NOR gate 250 is in turn connected to drive a reset circuit 252 and an inverter 254 connected to the clock input of a JK flip-flop 256. Reset circuit 252 includes a RC delay 258 and an inverter 260. The J input of flip-flop 256 is supplied by NAND gate 248. The circuitry of comparator means 238 is completed by lead 262 which supplies a resetting pulse to both the remaining inputs of triple-input NOR gate 250 and the reset input of flip-flop 256 whenever the cassette 16 (not shown in FIG. 7) of fluid metering device 2 is first inserted into the metering device control unit 4 (also not shown in FIG. 7).

The operation of comparator means 238 of FIG. 7 proceeds in generally the same fashion as the operation of comparator means 166 and 200 of FIG. 6. The insertion of the cassette into the metering device control unit, as discussed above, produces a pulse from cassette switch on lead 262, which pulse resets flip-flop 256 and momentarily switches the output of NOR gate 250 low to generate a RESET pulse at inverter 260. The RESET pulse clears binary counters 240 and 242. Thereafter, incoming RATE and FLAG pulses respectively clock the counters until one or the other of the counters reaches a binary count of twelve (1100), whereupon the $Q_2$ and $Q_3$ outputs of that counter simultaneously switch high. The associated AND gate 244 or 246 likewise switches high to drive the output of NOR gate 250 low, forcing inverter 254 high to clock flip-flop 256 and causing reset circuit 252 to generate a RESET pulse which resets the comparator means following the interval determined by RC delay 258. If, at the point NOR gate 250 is driven low, the count at the remaining binary counter has reached at least eight (1000), the $Q_3$ output thereof will be high and an "and" condition will appear at NAND gate 248. The consequent low output from NAND gate 248, which is supplied to the J input of flip-flop 256, produces a corresponding low Q output as the flip-flop is clocked, indicating the existence of an acceptable ratio between the RATE and FLAG pulses. Due to the fact that the $Q_2$ and $Q_3$ output stages of binary counters 240 and 242 are now employed to register the incoming pulse train counts, this ratio is a 8/12 or ⅔ ratio, as opposed to the 8/10 ratio of FIG. 6. Of course, where one binary counter 240 or 242 has not yet reached at least an eight count by the time the other counter reaches twelve, the low $Q_3$ output from the slower counter will produce a high signal from NAND gate 248 to the J input of flip-flop 256 when the flip-flop is clocked. The corresponding high Q output from the flip-flop then serves as an indication of an unacceptable deviation of the actual main stepping motor speed from the optimum or desired main stepping motor speed. The Q output can be removed from flip-flop 256 via lead 264 to yield a warning of fluid overor under-delivery conditions. If desired, the $\overline{Q}$ output may also be removed from flip-flop 256 via lead 266 and used as a second control or indicating signal by the microprocessor.

Figure 8:
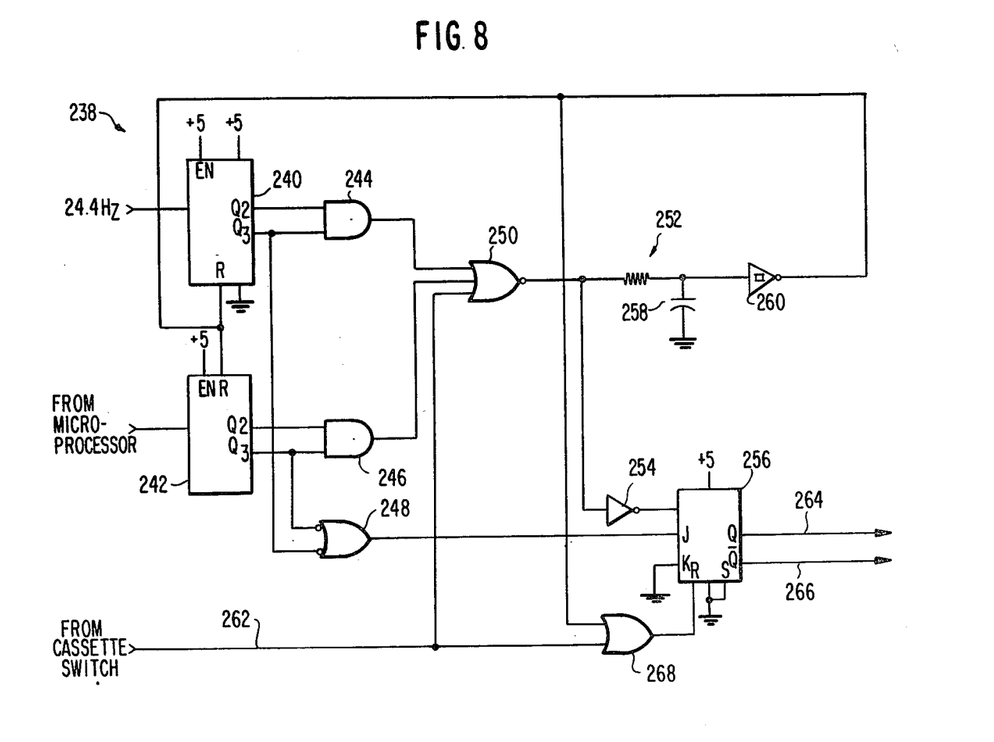
FIG. 8 is a third embodiment of a comparator circuit for use with the pump motor run-away prevention circuit of FIG. 6.

FIG. 8 illustrates yet another embodiment of the comparator means 200 of FIG. 6, wherein an OR gate 268 has been inserted in lead 262 of the comparator means. OR gate 268 is also supplied via lead 270 with the output of reset circuit 252. It can be seen that the RESET pulse occurring when either of the binary counters 240 or 242 reaches a twenty-four count acts to reset flip-flop 256, thereby preventing any spurious tripping of the flip-flop during the resetting of the binary counters.

The present invention has been set forth in the form of several preferred embodiments. Modifications to the pump motor run-away prevention circuit disclosed herein may nevertheless be made by those skilled in the art without departing from the spirit and scope of the present invention. For instance, the pump motor run-away prevention circuit may be accomodated for use with a main stepping motor which rotates in reciprocal fashion rather than in continuous fashion. That is, the main stepping motor 74 of FIGS. 1-3 can be designed to shift through incremental steps in a forward direction to turn cam 76 and reciprocate plunger 72 through its downward stroke, while the upward stroke of the plunger is accomplished by reversing the motor direction at the half-revolution point and shifting the motor back through the earlier incremental step positions in reverse order or fashion. In the reciprocating motor arrangement, slot 118 in flange 116 will align with LED 122 and photodetector 124 twice during each single pumping cycle, and the resulting FLAG pulses from optical interruptor module 120 will occur at a frequency equal to twice the pumping cycle frequency. Suitable adjustment of either the rate multipliers 136-140, or the first and second counters 148, 162 of the pump motor run-away prevention circuit, will produce a RATE pulse train having a frequency compatible with the doubled frequency of the FLAG pulses.

Other modifications to the pump motor run-way circuit of the present invention may be made as well by those skilled in the art, it being understood that all such modifications are considered to be within the purview of the appended claims.

What is claimed is:

1. An apparatus for monitoring the speed of a fluid pump motor which rotates under the command of a controller circuit to effect delivery of fluid from a fluid metering device and for generating an alarm signal whenever the actual motor speed deviates from a desired motor speed by more than a predetermined amount, said apparatus comprising:

sensing means for sensing the actual speed of the motor and for generating a first signal which represents the actual motor speed when the motor is rotating;

computing means connected to receive data input indicative of a desired fluid delivery rate and for generating a second signal representative of the desired motor speed necessary to achieve the desired fluid delivery rate;

comparator means for receiving said first and second signals and for comparing said first and second signals with one another in order to provide the alarm signal whenever the ratio of said first and second signals falls outside a predetermined range; and simultation means operable when the motor is stopped to supply said computing means and said sensing means with a first set of simulation signals which interrupt said computing means to prevent said second signal from being generated while causing said sensing means to generate said first signal such that said ratio of said first and second signals falls outside said predetermined range, said simulation means also operable to supply said computing means and said sensing means with a second set of simulation signals which prevent said sensing means for generating said first signal while permitting said computing means to generate said second signal such that the ratio of said first and second signals likewise falls outside said predetermined range.

2. An apparatus as set forth in claim 1, wherein said simulation means includes a microprocessor which also functions as part of the controller circuitry to generate command signals for the motor, said microprocessor operating to supply said first and second sets of simulation signals, and wherein said simulation means further includes a means for storing a malfunction signal when said comparator means fails to generate the alarm signal during operation of said simulation means.

* * * * *